United States Patent [19]

Coulter et al.

[11] Patent Number: 4,609,017

[45] Date of Patent: Sep. 2, 1986

[54] METHOD AND APPARATUS FOR TRANSPORTING CARRIERS OF SEALED SAMPLE TUBES AND MIXING THE SAMPLES

[75] Inventors: Wallace H. Coulter, Miami Springs; William F. Rothermel, Hollywood, both of Fla.

[73] Assignee: Coulter Electronics, Inc., Hialeah, Fla.

[21] Appl. No.: 541,603

[22] Filed: Oct. 13, 1983

[51] Int. Cl.[4] .............................................. G01N 1/14
[52] U.S. Cl. ........................................ 141/1; 141/11; 141/130; 141/83; 141/329; 422/100; 422/65; 73/864.21; 73/864.24
[58] Field of Search ..................... 141/1, 11, 21–28, 141/69, 83, 98, 130, 167, 168, 170, 271–273, 284, 329; 73/864.21–864.25; 366/208, 214, 209, 218; 422/65, 63, 100, 67; 436/47

[56] References Cited

U.S. PATENT DOCUMENTS

| | | | |
|---|---|---|---|
| 3,501,131 | 3/1970 | Grantham | 366/202 |
| 3,549,994 | 12/1970 | Rothermel | 324/71.1 |
| 3,575,692 | 4/1971 | Gilford | 422/65 |
| 3,614,434 | 10/1971 | Horwitz et al. | 73/864.22 X |
| 3,625,485 | 12/1971 | Adler | 366/216 |
| 3,768,526 | 10/1973 | Sanz et al. | 141/90 X |
| 3,872,730 | 3/1975 | Ringrose et al. | 73/864.23 |
| 3,883,305 | 5/1975 | Hoskins et al. | 141/130 X |
| 4,120,662 | 10/1978 | Fosslien | 73/425.6 |
| 4,147,250 | 4/1979 | Schulz | 198/412 |
| 4,170,798 | 10/1979 | Krumdieck | 141/130 X |
| 4,199,013 | 4/1980 | Reich et al. | 141/130 |
| 4,274,453 | 6/1981 | Lee | 141/1 |
| 4,311,484 | 1/1982 | Fosslien | 73/864.21 |
| 4,329,068 | 5/1982 | Neuner et al. | 366/214 |
| 4,342,341 | 8/1982 | Lee | 141/1 |
| 4,387,076 | 6/1983 | Cabrera et al. | 141/130 X |

FOREIGN PATENT DOCUMENTS 2095403 9/1982 United Kingdom .

Primary Examiner—Stephen Marcus
Assistant Examiner—Ernest G. Cusick
Attorney, Agent, or Firm—Gerald R. Hibnick

[57] ABSTRACT

A plurality of sealed blood sample tubes are housed in a rack and a plurality of these racks are vertically stacked, with the sample tubes lying horizontally. The racks are successively deposited onto a horizontal conveyor belt which is housed in and moves longitudinally on a table that rocks around its longitudinal axis to mix the samples in a semi-inverting mode as a rack is stepped from the stack to a sample aspiration station and/or thereat. The aspiration station preferably includes a sample segmenting and diluting valve and a sample identification reader. Aspiration is accomplished by pushing a sample tube partially out from the carrier rack and onto a seal piercing tip of the aspiration probe. The tube then is returned to the rack. The other tubes in that rack similarly are aspirated after the rack is stepped to align each tube with the aspiration probe, with table rocking and sampling mixing accompanying each advancing step of the rack. After a rack has advanced through the aspiration station, it is stacked out of the way.

28 Claims, 4 Drawing Figures

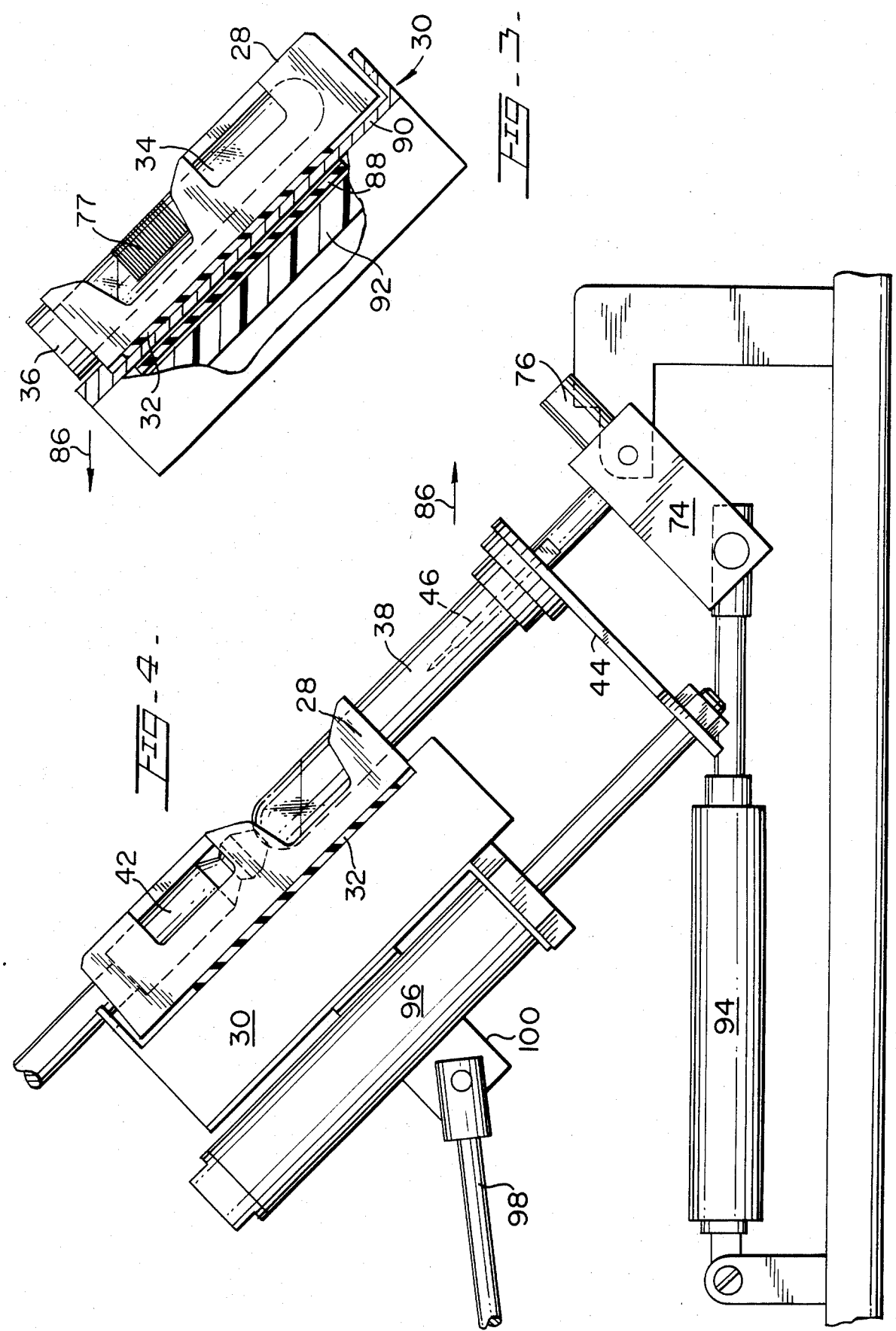

METHOD AND APPARATUS FOR TRANSPORTING CARRIERS OF SEALED SAMPLE TUBES AND MIXING THE SAMPLES

BACKGROUND OF THE INVENTION

This invention concerns a sample mixing and transport method and apparatus for samples in sealed containers, the containers being transported in groups in rack-type carriers. More specifically, this invention is directed toward the full automation of hematology analysers of the type which heretofore required the manual introduction of a blood sample held in an open-mouthed container. This goal of full automation is accomplished by transporting groups of sealed blood sample containers in racks to and from the sample aspiration station of the hematology analyzer and, while approaching the aspiration station and/or thereat, the samples are mixed by rocking the carrier rack.

Semi-automated hematology analyzers have been in common use for many years. U.S. Pat. No. 3,549,994 teaches such a semi-automated system for measuring a plurality of parameters of a whole blood sample. In using this system, the premixed blood sample is introduced manually into the system via an open-mouthed sample container, which is held up to an aspirating probe. Although this system offered a significant advance in the art when first sold in 1968 as the Coulter Counter ® Model S and there have been numerous subsequent improvements to this system over the past 15 years, the sample introduction has remained essentially unchanged. First, the sealed sample container is partially inverted several times manually to mix its contents, the sealing stopper then manually is removed, and then the open container is moved up into the aspiration tube. Not only does this procedure suffer from the various obvious drawbacks of manual handling, but also the opening of the whole blood container, which typically is under a small vacuum by virtue of the blood collecting technique, permits an aerosol to escape into the laboratory close to the technician who is operating the system. Such aerosol can contain blood related impurities and transmit disease, such as hepatitis.

The need for avoiding the manual opening of the sealed blood sample container has been recognized. U.S. Pat. No. 4,274,453 teaches a substantially manually fluid transfer device by which each sealed sample tube manually is placed upright into a free standing clamping gig which is provided with a vertically reciprocating aspiration probe having a seal penetrating tip. The probe with its tip is lowered manually into and through the sealed top of the sample container by a lever arm mechanism and motion which is like the well-known manual orange juice squeezer. The remote end of the aspiration probe feeds into an automated hematology analyzer. Besides its manual limitations and the one-at-a-time handling of the sample containers, this device does not accomplish sample mixing.

U.S. Pat. No. 4,387,076 teaches a substantially automatic sample feeding arrangement which receives sealed sample tubes, moves them one at a time to a seal piercing and sample aspiration station, and then discharges the used tubes. This sample feeding arrangement is mounted inside a sample analyzer of the type taught in previously mentioned patent 3,549,994, which without benefit of this invention would operate semi-automatically. Receipt of the sample tube at the in-feed station of this feeding arrangement initiates the repositioning of the tube to an aspiration station, which thereat enables all other handling steps of the tube, sample aspiration, and the full system cycle of the analyzer to cause it to be fully automated. This arrangement now is commercialized as the Coulter Counter ® Model S Plus V. Although this improvement is a significant step forward in sample handling, it does not provide for sample mixing. The sample containers need to be manipulated to mix the whole blood sample just prior to input of the tubes to the feeder mechanism.

The typical method for manually manipulating the sealed sample tube to attain adequate mixing of the whole blood constituents is for the technician to grasp the tubular container in her hand with the ends of the tube extending from opposite sides of the palm, adjacent the thumb or index finger and little finger, respectively. The technician then rotates her wrist through an arc approaching 180° many times to accomplish several semi-inversions of the tube. This mixing is not to be high speed, violent, or jerky, since the blood cells are fragile and not to be damaged by the mixing process, since cell trauma can affect the data results to be obtained by the hematology analyzer.

Bench-top sample tube mixers have been marketed for years and there are several simple commercial units. One unit primarily rolls the tubular sample container on its long axis and imparts slight end tilting action. Such arrangement does not simulate the manual mixing mode. Another device is a spinning vertical disk, to which the sample tubes are clipped in a radial array. Although such device does accomplish tube end inversion, it does not have the end reversing action of the human wrist movement. U.S. Pat. No. 3,625,485 teaches both the rotating as well as reversing direction or rocking movements for a few sealed sample tubes that are clipped onto a horizontal, rotating axis.

Another form of tube mixer is a tilting tray, which does simulate the manual mixing mode. One such tray is the Coulter ® Blood Mixer and is generally described in U.S. Pat. No. 3,501,131. The tray holds a plurality of sealed sample tubes and is rocked about its axis to simulate the manual semi-inversions. After sample mixing by any of these prior art mixers, each tube is removed separately from the mixing device, manually opened and then the sample contents are fed into the hematology analyzer. If the hematology analyzer is of the type of the aforementioned patent 3,549,994, the manually opened sample tube with its mixed sample is held up into the hollow tipped aspiration probe. However, if the analyzer is equipped with the automating feeder of patent 4,387,076, as above described, the manual opening is avoided.

The need for combining sample tube mixing with sample aspiration from a sealed sample container has been recognized and disclosed in the prior art. U.S. Pat. No. 4,120,662 discloses a free standing, self-programmed system in which individual sample tubes are placed horizontally into a vertically oriented pair of feed screws, such that each individual tube is moved slowly downward along the feed screws and, simultaneously, rotated around the long axis of the sample tube. Differential speed of the two feed screws will impart a limited amount of end lifting motion to the tubes. At the bottom of the downward path of the feed screws is a horizontally disposed and reciprocating aspiration needle which pierces the tube seal and then aspirates sample into a coupling line which feeds into a separately operating hematology analyzer. Although this system does combine the sample mixing and aspirating of the sample from a sealed container, it is a separate unit from the analyzer system and requires appreciable bench space, requires the sample tubes to be input individually, does not fully simulate the desired manual mixing mode, and has other limitations. For example, the horizontal spacing between the vertical feed screws must be kept constant; hence, all of the sample tubes being processed during any one period of time must be of the same exact length and also the same volume, since the diameter of the tube must be constant and is factory predetermined because of the pitch of the feed screws. However, it is common practice to collect blood samples in tubes of several different lengths and diameters and an optimized system should be able to receive sequentially any of the various diameter and length tubes, randomly.

United Kingdom patent application 820164, published on Sept. 29, 1982 as patent publication 2095403A discloses two forms of devices which combine sealed sample tube mixing and aspirating. One such device utilizes a form the vertically rotating mixing disk arrangement, previously mentioned, and adds to it a programmed aspiration station, for piercing the tube seal. A commercial form of this device is fitted with two mixing disks to increase throughput; one disk operates in a premix mode and the other disk provides final mixing and is being coupled to the aspiration station, with its seal piercing, reciprocating aspiration probe. Such device is sold as the Coulter ® CASH ™ system, in which the aspiration station is the input to a Coulter Counter ® Model S plus system, which is an improved version of the system taught in the previously described patent 3,549,994. Although built and operated as an integrated system—mixer, seal piercer and analyzer—the commercial version comprises two side-by-side units in which the aspiration station, in the mixing and aspirating unit, is coupled by a fluid line to the sample segmenting and diluting valve in the analyzer unit. The necessary length of this fluid line causes the amount of blood sample drawn from the sample tube to be greater than if the aspirating station was located within the analyzer unit and close to its segmenting, diluting valve. Also, the loading of the individual sample tubes on to the mixing disk and the capacity of the mixing disk are inherent limitations of this system.

The second device embodied in United Kingdom published Specification 2095403A has a greatly increased capacity and also is built into the body of the hematology analyzer. This embodiment uses a plurality of tube racks, each holding a plurality of sealed sample tubes. The racks are manually, removably secured to the periphery of a horizontal drum, such that each rack has its base against the periphery of the drum and the racks are spaced around the drum; hence, the longitudinal axes of the numerous sample containers radiate from the hub of the drum and the sealed ends of the sample tubes are remote from and facing away from the drum. To accomplish sample mixing, the drum rotates slowly to totally invert the racks and thus inverts the tops of the saple containers relative to their closed bottoms. A track system carries an aspirating needle over the length of the top of a rack, when it is positioned in one certain of the rotating drum determined positions. Thereupon, the needle sequentially is driven into each sample container aspirates some sample, is withdrawn from the container, and then is advanced horizontally to be positioned for insertion into the next container in that rack. Although this system has advantages over all of the mentioned prior art, it does require insertion and removal of the rack from the drum in a limiting manner. Its engineering design is somewhat complex. It and the previously disclosed first embodiment do not simulate the manual mixing mode.

The transporting of sample tubes in a plurality of racks, past a sampling station, is old in the art as evidenced by U.S. Pat. Nos. 3,575,692; 3,768,526 and 4,147,250. Generally, the sample racks are maintained in one plane, with the racks and the open mouthed sample tubes constantly remaining upright. Patent 3,575,692 teaches that the vertically disposed racks and their vertically held sample cups can be transported by way of feed elevators disposed on opposite sides of the sampling station. This patent does not teach the use of mixing or sampling by seal piercing as herein previously discussed, since the sample tubes are open to atmosphere at all times.

SUMMARY OF THE INVENTION

The present invention permits a totally integrated system of hematology analyzer, sample carrier transport, sample tube mixer which simulates the manual mixing mode, and tube seal piercer. This goal is accomplished by a simple, yet elegant, assembly which effectively has an unlimited capacity, with minimum of technician interaction at significantly spaced times. The sealed sample tubes are mounted in racks which are stacked vertically above an input elevator. The racks are stripped one at a time from the bottom of the stack and lowered by the elevator onto a combined conveyor belt and tilt table. The conveyor advances a rack until a first of its retained sample tubes is aligned with the aspiration station having a seal piercing sample probe. When the rack is advancing to the aspiration position and/or when the tube generally is aligned with the aspiration probe, the coneyor belt table rocks around its longitudinal axis to simulate the manual mixing mode. After adequate mixing, the conveyor table is locked with a sample tube in precise alignment with the aspiration probe, the table then being tilted "forward" so that the sealed tube end is significantly below its other end. Thereupon, the tube is pushed forward partly from the top of the carrier rack onto the seal piercing probe tip, for sample aspiration. After aspiration, the tube is returned fully into the rack, the transport table advances one step to place the next tube into aspiration position and, preferably, one or more mixing rockings is accomplished before the table again is locked into aspiration mode orientation. After each entire carrier of tubes has been processed, it is stepped along the table to an output elevator and, successively, the racks are stacked vertically out of the way. At a time and place during, or just prior to, sample aspiration, the identification of the sample is read automatically for correlation with that sample's parameter measurements. The aspiration probe is positioned next to the sample segmenting and diluting valve. At spaced times, the instrument operator can add several new racks of samples into the input stack and remove several already processed racks from the output stack.

BRIEF DESCRIPTION OF THE DRAWINGS

FIG. 3 is a side view taken along the line 3—3 of FIG. 2; and

FIG. 4 is a side view taken along the line 4—4 of FIG. 2.

DETAILED DESCRIPTION OF THE PREFERRED EMBODIMENT

Figure 1:
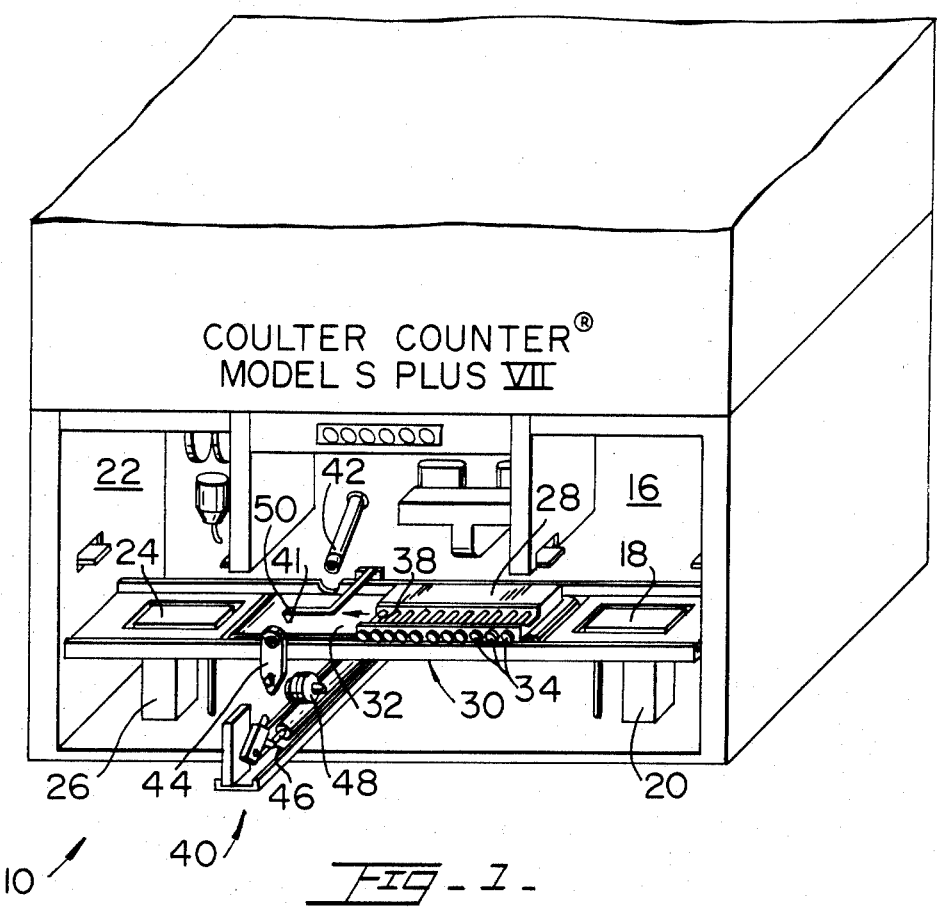
FIG. 1 is a perspective, somewhat pictorial, view of a hematology analyzer with the sample mixing and sample tube carrier transporting feature of this invention.

With reference to FIG. 1, there is shown, somewhat pictorially, the entire hematology analyzer 10, which preferably is of the Coulter Counter ® Model S Plus type, but that is not an essential limitation. The analyzer 10 has full capabilities for accomplishing multiparameter hematology analysis from whole blood samples. It contains electronic, pneumatic and fluid moving components, generally as taught in patent 3,549,994, as well as state of the art improvements, including but not limited to microprocessor control. A portion of the power supply and pneumatic system can be housed in one or more units below the laboratory bench top on which the analyzer body of FIG. 1 sits. It is the goal of this invention that the sample carrier transporting, tube seal piercing and sample mixing system be integrated fully into the body of the analyzer 10, physically as well as the program controls, pneumatics, electronics and fluid moving components; and this integration goal will be set forth in the preferred embodiment disclosed. However, the primary elements of the sample carrier transporting, seal piercing and sample mixing system are capable of being housed in a stand-alone module, with the aspirated sample then being fed from this module into the main body of the analyzer. Such module configuration would be useful for retrofit with older styles of analyzers.

Figure 2:
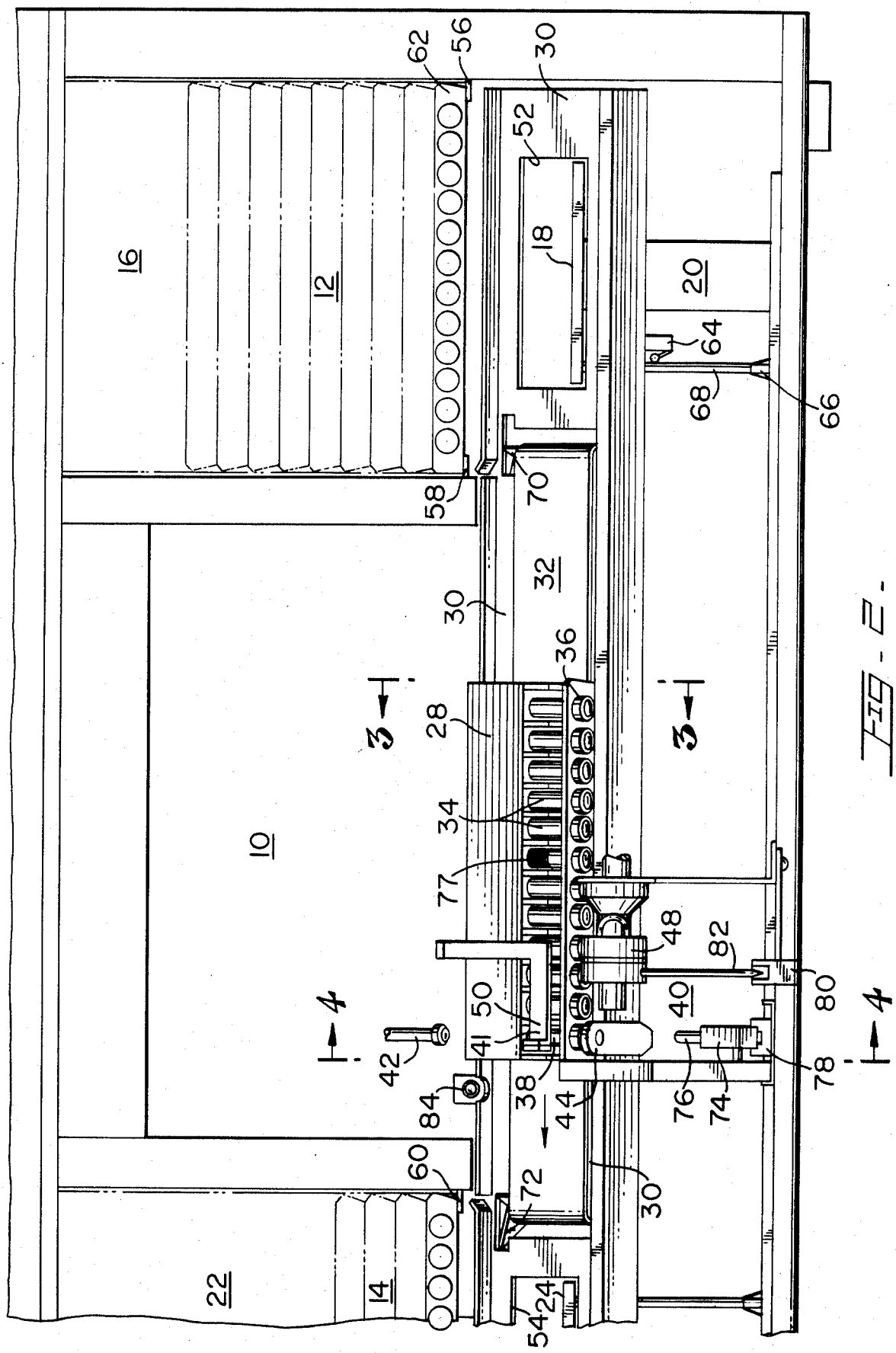
FIG. 2 is a front elevational view of a major portion of the carrier transporting and sample mixing structure of the invention.

As viewed from FIGS. 1 and 2, the right side of the analyzer 10 will be the sample tube carrier input side and the left side of the analyzer will be the tube carrier output side. For ease of illustration and interpretation, the stacks 12 and 15 of racks are shown only in FIG. 2 and not in FIG. 1. Conversely, FIG. 2 shows none of the body or components of the analyzer, a few of the components being shown, but not numbered in FIG. 1. Again with reference to FIG. 1, the input stack of racks or carriers 12 is in an input compartment 16, at the base of which is the platform 18 of an elevator mechanism 20. The output side of the system has a similar compartment 22, platform 24 and elevator mechanism 26. After the input side elevator 20 strips a carrier 28 from the bottom of the input stack, by a procedure to be described subsequently, that carrier is stepped leftward along a transporting and mixing table 30. The top of the table supports a conveyor belt 32 and there is more than sufficient friction between the bottom surface of the tube rack 28 and the belt 32 to accomplish leftward stepping of the carrier rack 28, each step being approximately the distance between the axial centers of the sealed sample tubes 34 in the rack.

To permit vertical movement of the elevator platforms 18 and 24, the belt 32 does not overlie the platforms. If there is not enough overlap of a carrier rack onto the belt 32, either at the infeed or outfeed positions relative to the platforms 18 and 24, so as to accomplish transfer from platform 18 to belt 32 and then to platform 24, there can be provided some simple "auxiliary" advancing mechanism (not shown in FIG. 1) to push or pull the carrier rack the small distance to and from adequate engagement with the conveyor belt 32.

It will be appreciated that the positions of several elements need to be monitored throughout the interactive operation of the entire cycling of rack movements, mixing, seal piercing, sampling, etc., etc. Such monitoring can be accomplished by various types of sensors, such as electrical and optical, well known in the art and commercially on the shelf. These sensors will not be all illustrated and their functions only sometime mentioned, since their use is well within the skill in the art.

The conveyor belt 32 can advance the carrier racks 28 in any angular position which the transporting table 30 has attained, as well as during rocking motion of the table 30. FIG. 1 shows the table horizontal, front to back, which is its orientation when receiving a rack from the stack 12, via the platform 18 and also when delivering a rack to the platform 24. In FIG. 2, the transporting table is shown tilted forward, at which position the sealed ends 36 of the tubes would be at least 45° below horizontal; whereas, a rearward tilting orientation shown in FIG. 3 is at least 90° reversed from FIG. 2. The stepping drive for the conveyor belt can be of conventional design and will not be detailed herein, except for brief mention with FIG. 3. Likewise, the table rocking mechanism, shown in FIG. 4, can be designed in various ways to achieve the simulation of the human wrist, semi-inversions of the sealed sample tubes. If the first or lead position sample tube 38 has not been mixed sufficiently by the time that it reaches alignment with the aspiration station 40, the conveyor belt 32 will stop stepping, but the table 30 will continue rocking. One way to determine adequate mixing is for the system to include a counter which can be pre-set to a minimum acceptable number of sample tube semi-inversions for the first to be aspirated tube 38. Thereafter, between aspirations of each subsequent tube, either before or when the rack is being advanced one step and/or when the next tube is aligned for aspiration, the transport table can be rocked a few times to ensure that the contents of the next tube are adequately mixed.

Alignment of the first sample tube 38 and each subsequent tube with the aspiration station 40 can be verified by a sensor 41. Thereupon, the transport table is rocked into the FIG. 4 shown forward orientation and locked thereat until the end of the aspiration cycle. Continuing with reference to FIG. 1, although FIGS. 2 and 4 show greater details and FIG. 1 does not show the lead positioned sample tube 38 in axial alignment with a push rod 42; when that alignment is achieved, as shown in FIGS. 2 and 4, the push rod 42 will push upon the bottom end of the sample tube, through an opening in the rack 28, and advance it partly out from the rack so that the stopper or sealed end 36 abuts a stripper bar 44, as shown in FIG. 4 only. If the aspiration probe tip 46 then also is aligned with the axis of the sample tube, the advancing by the push rod 42 will drive the sealed end 36 onto the probe tip, for penetration through the stopper. The aspiration probe is coupled by a short length of tube to the input of a sample segmenting and diluting valve 48, several forms of which are well known and one embodiment is taught in U.S. Pat. No. 4,152,391. Aspirated sample thereupon is processed by the components in the main portion of the hematology analyzer 10 to attain multiparameter blood data.

After sample aspiration from the first tube 38, the stripper bar 44 is driven toward the rear, to return the sample tube 38 back into its normal position in the carrier rack 28. Such tube movement strips the seal 36 from the probe tip 46. As well known in the art, the probe tip and the diluting valve then can be backflushed to eliminate the problem of sample carryover. Thereupon, the transport table will be advanced and rocked to present a next tube to the aspiration station 40 and the aligned push rod 42.

The mixing by rocking, stepping into aspiration alignment, and aspirating can continue until an entire rack of tubes has been processed. That rack then is advanced along the conveyor belt 32 until it overlies the elevator platform 24. By that time, a next-to-be-processed tube carrier can have been on the conveyor belt for a long enough time for its sample tube contents to be adequately mixed and its lead positioned tube to be close to alignment with the aspiration station 40. A plurality of racks of tubes thus can be processed without any human operator intervention or supervision. At any convenient time before the input stack 12 of carriers is depleted and/or the output compartment 16 becomes filled with processed racks, an operator can refill as well as empty the input and output compartments 16 and 22, respectfully. If a STAT sample is in need of processing, its tube can be loaded manually into the carrier just prior to the aspiration station, if its sample has been premixed; or, that STAT tube can be loaded into a carrier 28 at the bottom of the input stack and the tube contents will become mixed by the already discussed rocking table routine. Since such loading of a STAT tube usually would mean that another tube would have to be removed from its carrier, the system can be provided with a manual-STAT program and a manual-STAT aspiration probe, such probe being integral with the valve 48.

A sample tube transporting arrangement as thus far described can be enhanced by automated sample identification. To provide machine readable indicia on sample racks and on sample tube labels is well known in the art. The stepping of the racks 28 along the conveyor belt 32 and the pushing of the tubes partially from and back into the carrier provide more than sufficient movement, at appropriate speeds, for there to be utilized state of the art identification readers, such as an optical bar code reader or a magnetic character recognition reader. Such a reader 50 can be fixedly positioned over the path of the racks and the individual tubes and be in the same support as the alignment sensor 41.

At this juncture of the description of the preferred embodiment, the primary features of the method and apparatus have been disclosed. Reference to FIG. 2 now will help in emphasizing that which has been described, in coordination with other details of structure and operation. Looking at the transporting and mixing table 30, it will be appreciated that it extends over the elevator platforms 18 and 24 and, therefore, the table has cutouts 52 and 54 to enable the platforms 18 and 24 to be raised thereabove and come into contact with the position of the lowest carrier in the stacks 12 and 14 in the compartments 16 and 22, respectively. The elevators 20 and 26 can be operated by pneumatic cylinders, not shown. At the bottom of each compartment, underlying the bottom-most carrier, are four retractable support fingers, of which only the three fingers 56, 58 and 60 are illustrated.

When the elevator 20 raises the platform 18 into contact with the bottom-most rack 62 and then raises the rack slightly above the fingers, the fingers 56 and 58 are retracted automatically to allow that rack to proceed downward on the platform and be deposited on to the table 30, which then would be in the horizontal position. The fingers will return to their supporting orientation for the next following rack. One manner of implementing the retraction action of the fingers 56 and 58 and other elevator position determined responses by the apparatus can be by the tripping of a microswitch 64 by a camming piece 66 at the bottom of a follower element 68, which is attached to the bottom of the platform 18; the camming piece attaining the position of the microswitch when the platform is supporting the bottom-most rack in the stack 12. The support finger 60 and its not illustrated mate in the output compartment 22 are not automated, since they merely need to be able to pivot upward, temporarily out of the way when the platform 24 raises a rack into contact with and then above those fingers. One clear of the bottom surface of that rack, these fingers will spring back horizontally to support the rack and the elevator 26 can retract the platform.

Once a rack 28 is on the rocking table 30 at its right or input side, a position not shown in any of the FIGS., it might not sufficiently rest upon the conveyor belt 32 to be advanced leftward. Hence, a sprocket 70 is mounted at the right end of the conveyor belt and will catch onto and drive the bottom of the carrier until the carrier overlies the belt enough for frictional advancement. A similar sprocket 72 is at the outfeed end of the belt, to ensure that the carrier is fed properly onto the output platform 24. The sprockets 70 and 72 are rotated by the movement of the conveyor belt, via shafts at the ends of the belt.

FIG. 2 shows the rocking table in its forward position and locked in preparation for sample aspiration and/or sample identification; however, the lead-position sample tube 38 has not yet been pushed forward by the push rod 42 and therefore the stripper bar 44 also has not been advanced. The locking of the table and the immobilization of the belt are triggered by the lead-position tube 38 being aligned with the push rod 42. Such orientation is sensed by the alignment sensor 41, which deactivates the conveyor belt drive and locks up a detent, not shown, under the table.

The aspiration probe tip 46 is not visable in FIG. 2, but is shown in FIGS. 1 and 4. It is mounted in a pivotable block 74 which carries both the probe tip and, at right angles thereto, a backstop 76. In a preferred mode of operation, each sample tube axially is advanced twice by the push rod 42 and twice returned into the carrier by the stripper bar 44. A first axial forward movement and/or the return movement fully into the carrier permits sample identification by the reader 50. The second axial forward movement is for seal piercing and aspiration. During the reading step, the backstop 76 provides a backstopping function by being in an abutting position just forward of the stripper bar. During aspiration, as shown in FIG. 4, the block 74 is pivoted to place the aspiration probe tip 46 into axial alignment with the tube.

Although reading of sample identification and piercing of the tube seal easily could be accomplished in the same forward axial movement of the tube, or reading could be in either or both the forward and return movements, it is preferred to separate these steps as an economic feature. If the identification label is unreadable for any reason, it would be wasteful of sample aliquot, analyzer cycling time and reagents to process that sample. Hence, if the reader 50 signals a non-read condition in a separate step, before the aspiration probe tip 46 is aligned with the sample seal 36, then the entire sampling and analyzing cycles can be omitted for that tube. To contend with an apparently unreadable label, that tube can be ejected totally from the carrier by an ejection ram 84 positioned just beyond the aspiration station 40. For ease of illustration, only a sample tube in the middle of the rack in FIG. 2 and the sample tube shown in FIG. 3 are shown with a label 77, for example a label carrying bar coded indicia. A receiving basket, not shown, will catch the ejected tube, which then can be processed manually or otherwise handled. The ejection cycle also can be triggered by a fully accepted, aspirated and analyzed sample, if the analyzer were to "flag" an abnormal condition or parameter which might require further, prompt technician handling.

Various other safety and program signaling sensors are provided, but are within the skill of the art and are not needed to be described herein for a full understanding of the invention. Also, the label reading could be accomplished by other relative motion between the sample tube and reader. For example, the leftward movement of the conveyor belt, or causing the tube to be rotated around its longitudinal axis at the reading station, or having a movable reading head could each be acceptable modes of achieving relative motion for label reading either at or prior to the time that the sample tube reaches the aspiration station 40.

At the bottom of the arcuate path of the aspiration probe tip 46 is a backwash fluid receiving trough 78. Similarly, there is a backwash trough 80 below the manual-STAT aspiration probe 82. This manual-STAT probe will pivot forward when the segmenting valve 48 is in sample aspiration orientation. Backwash structures and functions for aspiration probes and sample valves are well known and taught, for example, in U.S. Pat. Nos. 3,976,429 and 4,148,859.

Turning next to FIG. 3, it is an elevational view, taken along the line 3—3 of FIG. 2, partly in section and partly broken away, looking from the end of the right side of the transport table 30 at a time when it is in the rearward orientation, i.e. when the tube seal 36 is above the other end of the tube. The arrow 86 is pointing to the front of the analyzer. The tube 34 is seated fully in the carrier 28, with the top side of the conveyor belt 32 in frictional engagement with the bottom surface of the carrier. Since the belt 32 is mounted as an endless track, it has a return portion 88 underlying the top surface 90 of the table 30. Although any one of many belt drives could be employed, a simple frictional, incremental form has proved effective. A pusher block 92 is cammable upward against the return belt portion 88 as it pushes it in the direction outward from the plane of the drawing, i.e. rightward with reference to FIGS. 1 and 2, to cause the upper surface 32 of the belt to advance the carrier in the proper leftward direction of FIGS. 1 and 2. The pusher block 92 is programmed to advance a distance slightly more than the desired stepping distance between adjacent tubes in the carrier and then it returns to its original position, for a next reciprocating movement. During the return movement of the pusher block, into the plane of FIG. 3, the camming is removed and the belt is not moved. The alignment position sensor 41 signals a stop pushing command to the block, to stop it and thus to release it from its cammed orientation, and enable it to return to its start-to-push "home" position.

The FIG. 4 forward orientation of the transport table 30 is shown also in FIG. 2; however, FIG. 4 shows the component aspiration position of the tube 38, the push rod 42, the stripper bar 44, the aspiration probe 46, and the pivotable block 74. Also shown is: a pneumatic cylinder-driver 94, which is coupled to the pivotable lock 74, to effect the positioning of the probe 46, or the backstop 76; a similar driver 96 coupled to the stripper bar 44 for driving the sample tube back into the carrier after aspiration; and the end of another driver 98, which is pivotably coupled to a support and direction translator 100 of the tilt table 30. Generally horizontal reciprocation of the driver 98 translates into arcuate movement of the support 100, thereby rocking the table at least 45° above and below horizontal.

The primary and many secondary features of construction and operation of this sample carrier transport and mixing, with sealed tube piercing and aspiration system have been illustrated and described to the extent that those skilled in the art should be enabled not only to understand the embodied invention, but also to practice same without undue experimentation and development. Variations and substitutions of equivalents are capable of being made without departing from the spirit and scope of the invention as defined in the appended claims.

What we seek to be protected by United States Letters Patent is:

1. A method for transporting carriers of sealed sample tubes, said tubes having sample material therein and there being a tube seal sealing one end of each tube, mixing the sample material in the tubes and piercing the tube seals for feeding of the sample material into a sample analyzer, each carrier holding a plurality of the sample tubes, said method comprising the steps of: advancing each of a series of the carriers along a longitudinal and substantially horizontal path from an input location to an output location, there being a seal piercing station between those locations; rocking the path around its longitudinal and substantially horizontal axis such that the sample tubes undergo a plurality of partial inversions during which the sealed end of each tube is rocked above and below the other end of the tube; said rocking being accomplished a plurality of times and in a sufficient manner for the sample material to be adequately mixed just prior to seal piercing; and stopping said advancing of each of the carriers at the seal piercing station for a time duration sufficient for seal piercing and sample feeding into the analyzer; said rocking being accomplished during at least one of said advancing and stopping steps.

2. The method of claim 1 which further includes the step of placing the carriers on the path such that the sample tubes are generally horizontal, with the longitudinal axis of each tube lying generally transverse to the longitudinal axis of the path.

3. The method of claim 2 which further includes the steps of stacking the carriers horizontally in a vertical stack above the input location and sequentially depositing each carrier onto the path at the input location.

4. The method of claim 3 which further includes the step of removing the carriers from the output location and stacking them horizontally in a vertical stack proximate to the output location.

5. The method of claim 1 further including the step of coordinating said advancing, stopping and rocking steps such that each tube is advanced sequentially advanced to the seal piercing station and there is attained a seal piercing orientation in which the sealed end of the tube is held significantly lower than the other end of the tube.

6. The method of claim 1 which further includes the steps of positioning and holding each sample tube partially out from its normally held position in the carrier, such positioning being accomplished at the seal piercing station and by axial translation of the sample tube.

7. The method of claim 6 in which the seal piercing station includes a probe with a seal piercing tip, said method further including the step of orienting the piercing tip such that said steps of positioning and holding each sample tube enables the seal to be pierced by the tip.

8. The method of claim 7 in which the seal piercing station is part of a sample aspiration station and the piercing tip feeds into an aspiration line coupled to a sample segmenting and dilution valve, said method further including the step of feeding the sample material from the tube into the valve by short coupling means, such that a minimal amount of sample material is aspirated for analyzing.

9. The method of claim 6 in which the sample tubes carry machine readable indicia, said method further including the steps of returning the tube from its partially out position to its normally held position in the carrier and reading the indicia during at least one of said positioning, holding out, and returning steps.

10. The method of claim 9 further including the step of ejecting selected sample tubes completely from the carrier when the carrier has advanced any such selected tube to a position along the path between the seal piercing station and the output location.

11. The method of claim 10 further including the steps of determining that a sample tube requires ejecting such determination being accomplished during said step of reading, and inhibiting feeding of the sample material to the analyzer.

12. The method of claim 1 further including the step of ejecting selected sample tubes completely from the carrier when the carrier has advanced any such selected tube to a position along the path between the seal piercing station and the output location.

13. The method of claim 1 in which said rocking approximates 90°.

14. The method of claim 1 in which said rocking exceeds 90°.

15. An apparatus for transporting carriers of sealed sample tubes, said tubes having sample material therein and there being a tube seal sealing one end of each tube, mixing the sample material in the tubes and piercing the tube seals for feeding the sample to an analyzer, each carrier capable of holding a plurality of the sample tubes, said apparatus comprising: a table having a longitudinal and substantially horizontal axis, said table being constructed and arranged to be rocked around its longitudinal and substantially horizontal axis, one longitudinal end of said table being its carrier input end and the other longitudinal end being its carrier output end; carrier conveyor means supported by said table and constructed and arranged for conveying said tube carriers over the surface of said table from proximate said input end to proximate output end, said tube carriers and said sealed sample tubes being horizontally aligned for movement on said carrier conveyor means, said conveyor means being rocked whenever said table is rocked and thereby rocking any carriers thereon and the sample tubes held therein; tube seal piercing means mounted adjacent to said table at a location between its said input and output ends; drive means for rocking said table and advancing said conveyor means, said drive means being constructed and arranged such that the sample tubes in a carrier on the conveyor will undergo a plurality of partial inversions during which the sealed end of each tube is rocked above and below the other end of the tube for sample mixing, said drive means further being constructed and arranged to advance a carrier on said conveyor means to bring the sample tubes into substantial alignment with said seal piercing means and then for stopping said conveyor means for a time duration sufficient for seal piercing, said drive means also being constructed and arranged to effect the table rocking during at least one of the conveyor advancing and the conveyor stopping time durations.

16. The apparatus of claim 15 which further includes carrier stacking compartments proximate to said input and output ends, said compartments being constructed and arranged for storing a plurality of said carriers with the sample tubes such that the sample tubes have their longitudinal axes generally horizontal.

17. The apparatus of claim 16 which further includes carrier transfer mechanism for transferring the tube carriers one at a time from the input end stacking compartment onto said table in a generally horizontal orientation, said table then being mounted in a generally horizontal orientation.

18. The apparatus of claim 15 in which said seal piercing means is mounted below the level attained by the tubes when each tube is advanced into substantial alignment with said seal piercing means, said table being constructed to be held in a forward rocked position with the sealed tube end being below horizontal and said seal piercing means being constructed to be held inclined for axial alignment with the longitudinal axis of the sample tube.

19. The apparatus of claim 18 further including sample tube positioning means for positioning and holding a sample tube partially out of and forward of its carrier, after that tube has been placed into axial alignment with said seal piercing means, to thereby drive the sealed tube end into the seal piercing means, such that the tube seal is pierced.

20. The apparatus of claim 15 in which said seal piercing means is constructed to receive sample material from the sample tube and feed the sample material directly to a sample segmenting valve via a coupling of short length.

21. The apparatus of claim 20 in which said seal piercing means and said sample segmenting valve are housed in a sample analyzer.

22. The apparatus of claim 15 in which the entirety of said apparatus is housed within and closely coacts with a hematology analyzer.

23. The apparatus of claim 15 which further includes indicia reading means mounted along a path of movement of said sample tubes.

24. The apparatus of claim 23 in which said path of movement of the tubes includes at least one of the longitudinal movement of the conveyor means and an axial movement of a sample tube when it is in substantial alignment with said seal piercing means.

25. The apparatus of claim 15 further including ejecting means for ejecting a sample tube completely from said carrier at a position that tube attains between said seal piercing means and said output end of said table.

26. The apparatus according to claim 15 in which said table is constructed to rock approximately 90°.

27. The apparatus according to claim 15 in which said table is constructed to rock at least 90°.

28. The apparatus according to claim 15 in which said drive means includes structure for advancing said carriers from said input end to said conveyor means and also sensor means for detecting alignment of each tube with said tube seal piercing means for thereupon stopping said conveyor means.

* * * * *

UNITED STATES PATENT AND TRADEMARK OFFICE
CERTIFICATE OF CORRECTION

PATENT NO. : 4,609,017
DATED : Sep. 2, 1986
INVENTOR(S) : Wallace H. Coulter and William F. Rothermel It is certified that error appears in the above—identified patent and that said Letters Patent is hereby corrected as shown below:

Column 1, line 13, "analysers" should be --analyzers--.
Column 3, line 33, "plus" should be --Plus--; line 62, "saple" should be --sample--.
Column 4, line 39, "coneyor" should be --conveyor--.
Column 5, line 42, "15" should be --14--.
Column 8, line 16, "One" should be --Once--.
Column 9, line 21, "and reader" should be --and a reader--.
Column 10, line 66, "advanced" (second occurrence) should be deleted.

Signed and Sealed this

Second Day of December, 1986

Attest:

DONALD J. QUIGG

*Attesting Officer*  *Commissioner of Patents and Trademarks*